(12) United States Patent
Hsu et al.

(10) Patent No.: US 9,963,742 B2
(45) Date of Patent: May 8, 2018

(54) KIR3DL1 ALLELE CLASSIFICATION KIT AND METHOD

(71) Applicant: MEMORIAL SLOAN-KETTERING CANCER CENTER, New York, NY (US)

(72) Inventors: Katharine Hsu, New York, NY (US); Jeanette Boudreau, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 275 days.

(21) Appl. No.: 14/776,581

(22) PCT Filed: Mar. 13, 2014

(86) PCT No.: PCT/US2014/025292
§ 371 (c)(1),
(2) Date: Sep. 14, 2015

(87) PCT Pub. No.: WO2014/151251
PCT Pub. Date: Sep. 25, 2014

(65) Prior Publication Data
US 2016/0040237 A1 Feb. 11, 2016

Related U.S. Application Data

(60) Provisional application No. 61/791,013, filed on Mar. 15, 2013.

(51) Int. Cl.
*C12Q 1/68* (2018.01)
(52) U.S. Cl.
CPC ......... *C12Q 1/6883* (2013.01); *C12Q 1/6881* (2013.01); *C12Q 2600/112* (2013.01); *C12Q 2600/118* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

2011/0129830 A1 6/2011 Ladner et al.
2012/0003633 A1 1/2012 Kuijpers et al.

OTHER PUBLICATIONS

Boulet; et al., "A combined genotype of KIR3DL1 high expressing alleles and HLA-B*57 is associated with a reduced risk of HIV infection", AIDS (Jul. 2008), 22(12):1487-91.

International Search Report and Written Opinion, from the Korean Intellectual Property Office dated Aug. 6, 2014, for International Application No. PCT/US2014/025292 (filed Mar. 13, 2014), 16 pgs.
"*Homo sapiens* KIR3DL1 gene for killer cell immunoglobulin-like receptor, KIR3DL1*004new allele, exons 1-9", NCBI, GenBank accession No. FN649468.1 (Feb. 23, 2010), 3 pgs.
Pelak; et al., "Number variation of KIR genes influences HIV-1 control", PLoS Biol. (Nov. 2011), 9(11): e1001208.
Thananchai; et al., "Cutting Edge: Allele-specific and peptide-dependent interactions between KIR3DL1 and HLA-A and HLA-B", J Immunol (Jan. 2007), 178(1):33-7.
Database GenBank [online], Accession No. AF262968, 2001, [date of retrieval: Jan. 11, 2018], URL, https://www.ncbi.nlm.nih.gov/nuccore/13560440?sat=4&satkey=39367470.
Database GenBank [online], Accession No. AF262969, 2001, [date of retrieval: Jan. 11, 2018], URL, https://www.ncbi.nlm.nih.gov/nuccore/13560442?sat=4&satkey=39367471.
Database GenBank [online], Accession No. AF262970, 2001, [date of retrieval: Jan. 11, 2018], URL, https://www.ncbi.nlm.nih.gov/nuccore/13560444?sat=4&satkey=39347472.
Database GenBank [online], Accession No. AF262971, 2001, [date of retrieval: Jan. 11, 2018], URL, https://www.ncbi.nlm.nih.gov/nuccore/13560446?sat=4&satkey=39367473.
Database GenBank [online], Accession No. AF262973, 2001, [date of retrieval: Jan. 11, 2018], URL, https://www.ncbi.nlm.nih.gov/nuccore/AF262973.
Database GenBank [online], Accession No. AY760035, 2004, [date of retrieval: Jan. 11, 2018], URL, https://www.ncbi.nlm.nih.gov/nuccore/AY760035.1.
Gardiner et al., "Different NK cell surface phenotypes defined by the DX9 antibody are due to KIR3DL1 gene polymorphism," Journal of Immunology, 166, pp. 2992-3001 (2001).
Halfpenny, I., et al., "Investigation of killer cell immunoglobulin-like receptor gene diversity: IV. KIR3DL1/S1," Human Immunology, 65, pp. 602-612 (Mar. 2004).
Shilling et al., "Allelic polymorphism synergizes with variable gene content to individualize human KIR genotype," Journal of Immunology, 168, pp. 2307-2315 (2002).
Yawata et al., "Roles for HLA and KIR polymorphisms in natural killer cell repertoire selection and modulation of effector function," Journal of Experimental Medicine, vol. 203, No. 30, pp. 633-645 (Mar. 20, 2006).

*Primary Examiner* — David C Thomas
(74) *Attorney, Agent, or Firm* — Foley & Lardner LLP

(57) ABSTRACT

Disclosed herein are single nucleotide polymorphisms (SNPs) characteristic of functional subgroups of KIR3DL1. Also disclosed herein are methods for classifying KIR3DL1 alleles by using a series of oligonucleotide primers and PCR reaction conditions uniquely designed to identify group-specific SNPs from genomic DNA. The compositions and methods disclosed herein are useful in clinical settings and research laboratories, and enable prospective assessment of prognoses of various diseases and selection of most appropriate donors for HCT.

28 Claims, 4 Drawing Sheets

KIR3DL1 ALLELE CLASSIFICATION KIT AND METHOD

CROSS REFERENCE TO RELATED APPLICATION

This application claims the benefit of priority from U.S. Provisional Application No. 61/791,013, filed Mar. 15, 2013, the entire contents of which are incorporated herein by reference.

STATEMENT REGARDING FEDERALLY SPONSORED RESEARCH OR DEVELOPMENT

This invention was made with Government Support under Contract Nos. AI069197, HL088134, awarded by the National Institutes of Health. The Government has certain rights in this invention.

FIELD OF THE DISCLOSURE

This disclosure generally relates to kits and methods for classifying KIR3DL1 alleles.

BACKGROUND ART

Epistatic interactions between subtypes of KIR3DL1 and its ligand, HLA-B, predict for differential outcomes in patients with HIV (Martin et al., Nature Genetics 39:733-740 (2007)) and undergoing hematopoietic stem cell transplantation (HCT) (Giglio et al. (November 2012)). Functional groups of KIR3DL1 predict for high- and low-inhibitory interactions with HLA-Bw4 and correlate with clinical outcomes in HIV and leukemia patients undergoing hematopoietic cell transplantation (HCT) (Martin et al., Nature Genetics 39:733-740 (2007); Giglio et al. (November 2012)). The 59 known inhibitory alleles have previously been classified into three subgroups based on the density with which they are expressed on the surface of NK cells (Gardiner et al., Journal of Immunology 166:2992-3001 (2001); Pando et al., Journal of Immunology 171:6640-6649 (2003); Yawata et al., J Exp Med 203). A group of KIR3DL1 alleles that encode the activating KIR3DS1 molecules accounts for an additional 12 alleles of KIR3DL1. While HLA-B alleles can be readily identified, a simple and cost-effective protocol for KIR3DL1 allele assessment is yet to be developed in order to translate the research findings into clinical practice.

SUMMARY OF THE DISCLOSURE

By aligning the coding sequences of the 71 known alleles of KIR3DL1, the inventors have identified single nucleotide polymorphisms (SNPs) unique to functional subgroups of KIR3DL1. By designing a series of unique oligonucleotide primers and PCR reaction conditions, these group-specific SNPs can be amplified from genomic DNA. The primer sets and methods disclosed herein are useful for classifying KIR3DL1 alleles in an efficient manner, and can be easily adopted by clinics and research laboratories to enable prospective assessment of prognoses for HIV and HCT, and retrospective analyses on the role of KIR3DL1 alleles in disease processes. As the relationships between KIR3DL1 and disease are further deciphered, allotyping of KIR3DL1 will be relevant in establishing prognoses. Diseases where HLA is deregulated, including but not limited to cancer, inflammatory bowel disease, conditions or infections associated with HIV, cytomegalovirus, hepatitis B virus, human papillomavirus and influenza, will likely be influenced by compound allotypes of KIR3DL1 and HLA-B. For allergenic HCT for acute myelogenous leukemia patients and HIV patients, selection of the most appropriate stem cell donor can be informed by performing KIR3DL1 allele typing.

BRIEF DESCRIPTION OF THE DRAWINGS

Figure 1:
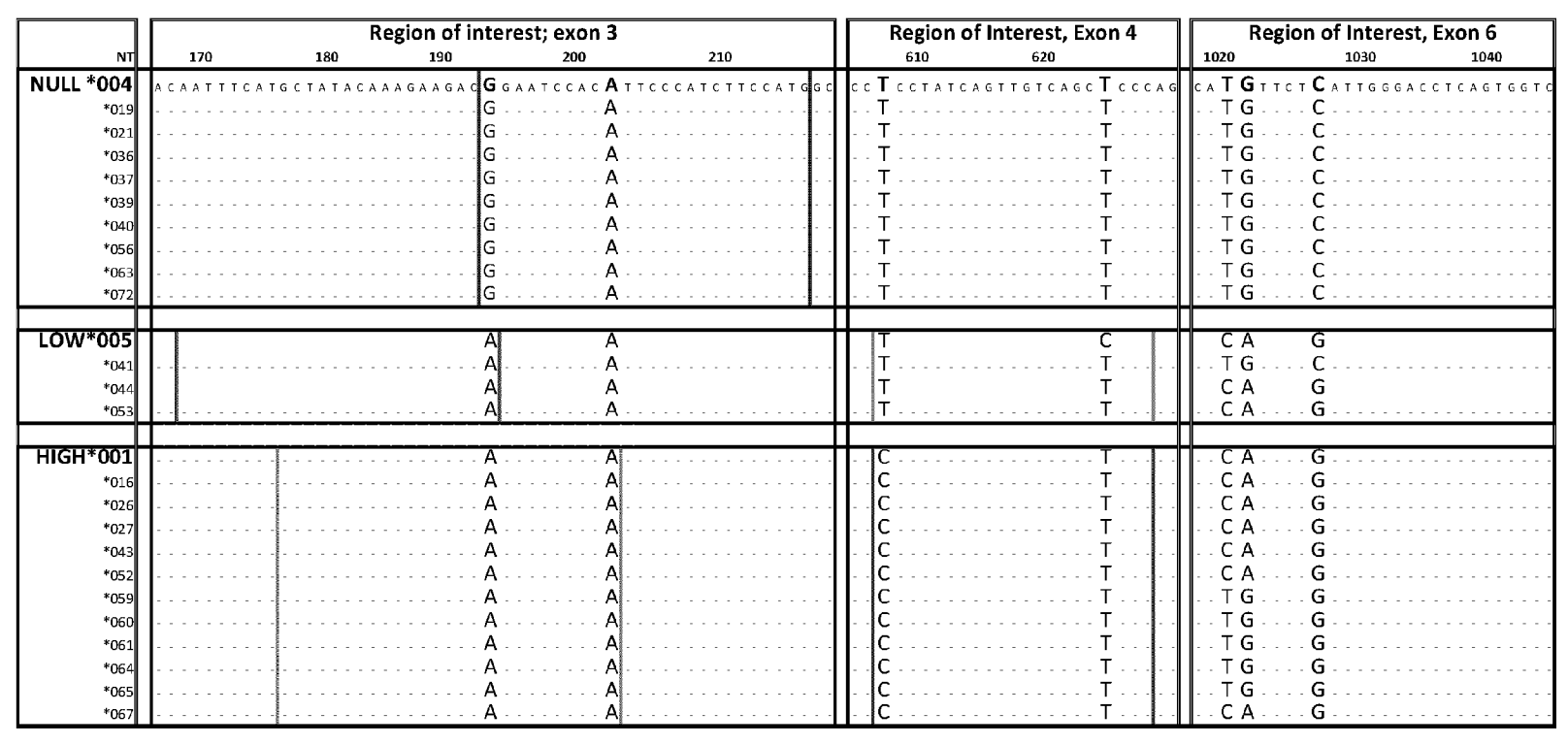
Figure 1:
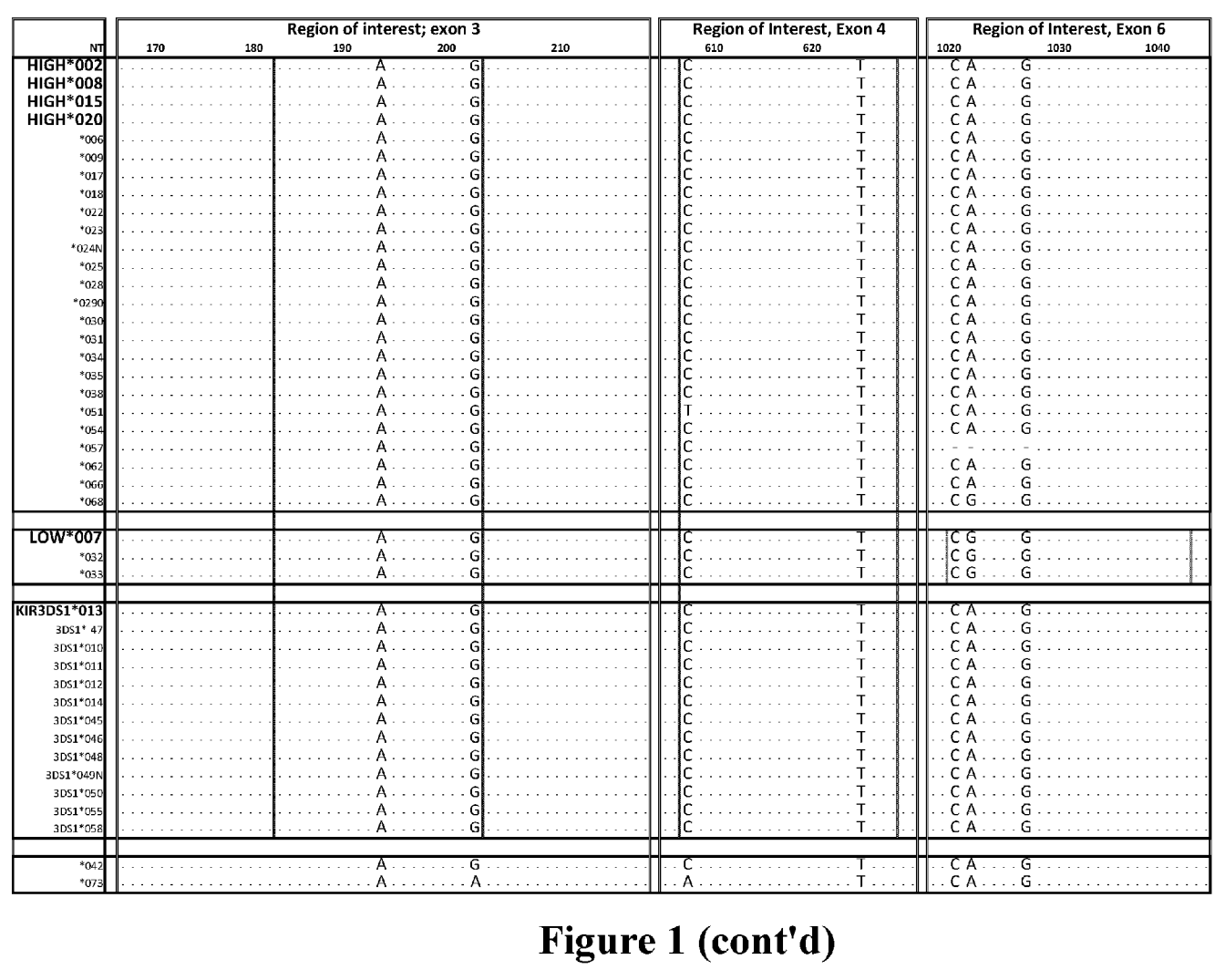

FIG. 1. Alignment and grouping strategy for KIR3DL1 alleles. The 11 most common alleles of KIR3DL1, each present with >1% frequency and shown in bold, were aligned and stratified according to their known characteristics of interaction with HLA-Bw4. Three polymorphic sites, present in exons 3 and 4 allowed for the stratification of alleles into four functional subgroups. An additional SNP, present in exon 7, enabled the creation of a reaction to allow for the identification of KIR3DL1*007, an allele previously characterized as LOW, but amplified among the 015-group high alleles. Subsequently, the remaining 59 known KIR3DL1 allelic sequences were stratified according to sequence homology with high-frequency alleles at these SNPs. Nucleotides that do not differ from the sequence of NULL*004 are shown as dashes and SNPs considered in primer designed are designated in bold typeface. Finally, the binding sites for each primer are shown in bold boxes. Primers that bind to a region conserved among KIR3DL1 alleles are not shown. The sequences shown in the various regions are assigned with the following SEQ ID NOS: Region of interest in exon 3—NULL*004 group, SEQ ID NO: 1; Low*005 group, SEQ ID NO: 2; High *002 group, SEQ ID NO: 3; Region of interest in exon 4—NULL*004 group, SEQ ID NO: 4; Low*005 group, SEQ ID NO: 5; High *001 group, SEQ ID NO: 6; *073, SEQ ID NO: 7; Region of interest in exon 7—NULL*004 group, SEQ ID NO: 8; Low*005 group, SEQ ID NO: 9; High *001 group, SEQ ID NO: 10; Low*007, SEQ ID NO: 11.

DETAILED DESCRIPTION

Figure 2:
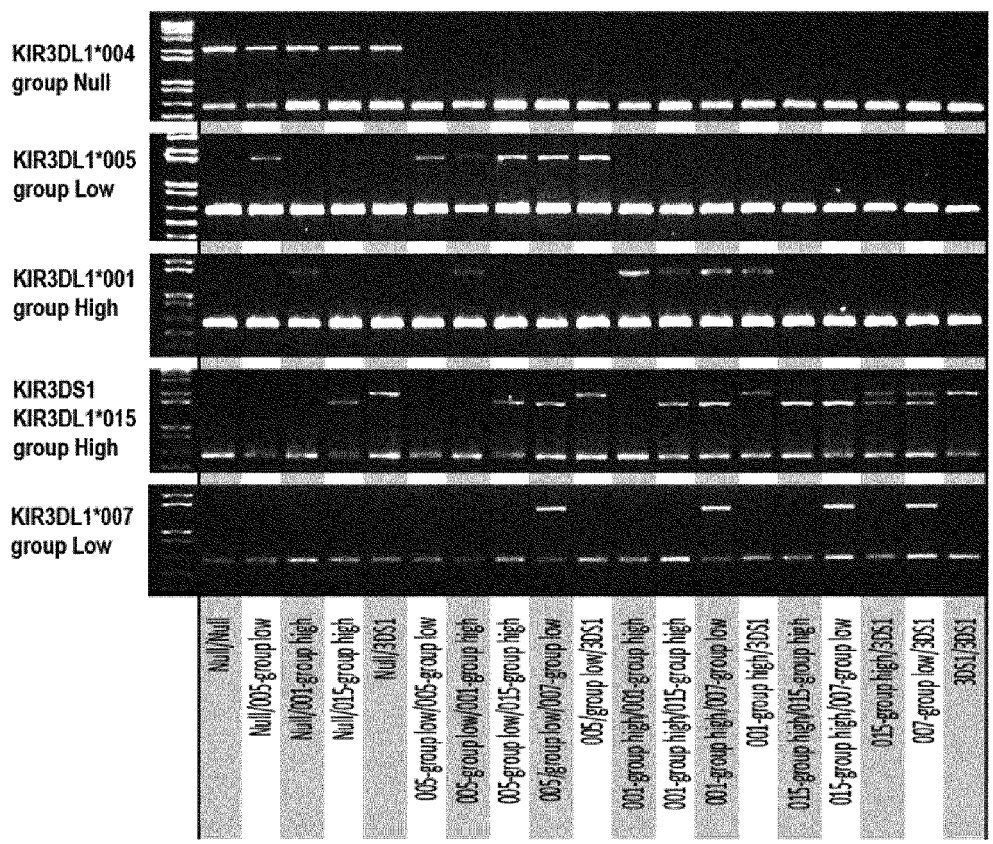
FIG. 2. Allele subgroup analysis is consistent with sequencing data. KIR3DL1 gene content from DNA derived from PBMCs of healthy, unrelated donors was determined by genomic sequencing. Subsequently, KIR3DL1 allele subgroup analysis was performed. Two reactions identify null and *007-group lows based on unique SNPs. Three additional reactions subdivide alleles into the remaining groups: 005-group low alleles and high alleles, subdivided as 001- and 015-group alleles. Validity of KIR3DL1 allotyping was confirmed by comparing allotyping results with sequence-based typing for 174 unrelated donors.

This disclosure provides kits and methods for classifying KIR3DL1 alleles based on polymerase chain reactions (PCR).

Classification of KIR3DL1 Alleles

By "classifying KIR3DL1 alleles", it is meant that by using the kit and the PCR-based methods disclosed herein, the allelic types of the KIR3DL1 alleles in a subject can be determined, and the functional subgroup KIR3DL1 assignments can be deduced.

In accordance with this disclosure, there are four allelic types for KIR3DL1: KIR3DL1-h, KIR3DL1-l, KIR3DL1-n, and KIR-3DS1. These four allelic types are also referred to herein as "allelic subgroups" for KIR3DL1.

A "KIR3DL1-h" or "KIR3DL1-high"("h" for "high"), as used herein, refers to an allele which expresses the KIR3DL1 receptor at high densities on the cell surface of NK cells detectable by cell surface staining using an antibody directed to KIR3DL1 receptor (such as Z27 or DX9), or an allele which is yet to be characterized for surface staining but shares substantial sequence similarity to an allele which expresses the KIR3DL1 receptor at high densities on the cell surface of NK cells detectable by cell surface staining. By "substantial sequence similarity", it is meant that the relevant sequences share at least about 90%, 95%, 98%, 99% or higher identity at the nucleotide level, or at least about 90%, 95%, 98%, 99% or higher similarity or identity at the amino acid level. KIR3DL1 alleles that are considered herein to be a KIR3DL1-h allele include KIR3DL1*001, *002, *008, *015, *020, *033, and *052, all of which have been characterized by cell surface staining; as well as KIR3DL1*009, *016, *043, *067, *026, *034, *035, *022, *017, *066, *029, *038, *025, *054, *018, *051, *068, *023, *028, *062, *030, *024N, *031, *042, and *057, which are yet to be characterized for surface staining but share substantial sequence similarity to a KIR3DL1-h allele characterized by high density cell surface staining.

A "KIR3DL1-l" or "KIR3DL1-low" allele ("l" for "low") as used herein, refers to an allele which expresses the KIR3DL1 receptor at low densities on the cell surface of NK cells detectable by cell surface staining (e.g., using Z27 or DX9), or an allele which is yet to be characterized for surface staining but shares substantial sequence similarity to an allele which expresses the KIR3DL1 receptor at low densities on the cell surface of NK cells detectable by cell surface staining. KIR3DL1 alleles that are considered herein to be a KIR3DL1-l allele include KIR3DL1*005, *007, and *053, all of which have been characterized by cell surface staining; as well as KIR3DL1*044, and *041 which are yet to be characterized for surface staining but which share substantial sequence similarity to a KIR3DL1-l allele characterized by low density cell surface staining.

A "KIR3DL1-n" or "KIR3DL1-null" allele ("n" for "null"), as used herein, refers to an allele which expresses KIR3DL1 molecules retained intracellularly and not detectable by cell surface staining (e.g., using Z27 or DX9), as well as an allele which has not been characterized by surface staining but shares substantial sequence similarity to a KIR3DL1-n allele characterized by low density cell surface staining. KIR3DL1 alleles that are considered herein as a KIR3DL1-n allele include KIR3DL1 *004, *019, and *056 (characterized by lack of surface staining); as well as KIR3DL1 *021, *036, *037, *039, *056, *072, *062, and *040 (yet to be characterized by surface staining).

A "KIR3DS1" allele expresses KIR3DS1 molecules, detectable by surface staining with Z27 but not DX9. KIR3DS1 alleles include but are not limited to KIR3DS1*013, *047, *010, *011, *012, *014, *045, *046, *048, *049N, *050, *055, and *058.

Essentially, the primers and PCR reactions disclosed herein permit allelic identification for the maternal and paternal KIR3DL1 alleles in a subject, without requiring conventional sequencing analysis. Once the KIR3DL1 allelic types are determined for the maternal and paternal alleles in a subject, the subject can be assigned to one of the following functional KIR3DL1 subgroups based on the combination of the subject's maternal and paternal alleles:

| KIR3DL1 Functional Subgroups | KIR3DL1 Allele Combinations |
|---|---|
| KIR3DL1-H | KIR3DL1-h/-h, or KIR3DL1-h/KIR3DS1 |
| KIR3DL1-L | KIR3DL1-l/-l, KIR3DL1-l/-h, or KIR3DL1-l/KIR3DS1 |
| KIR3DL1-N | KIR3DL1-n/-n, KIR3DL1-n/-h, KIR3DL1-n/-l, or KIR3DL1-n/KIR3DS1 |

Grouping Strategy and Primer Design

Oligonucleotide primers are provided herein for amplifying regions of KIR3DL1 alleles containing single nucleotide polymorphisms (SNPs) specific for the KIR3DL1-h, -l, -n and KIR3DS1 alleles, respectively.

The term "single nucleotide polymorphism" is well-understood in the art as referring to a nucleic acid sequence variation which occurs when a single nucleotide in the genome differs between members of a biological species. In the context of this invention, the inventors have identified SNPs that are unique to KIR3DL1-h, -l, -n and KIR3DS1 alleles, respectively, and that permit design of primer pairs to generate PCR products which distinguish among the KIR3DL1 alleles.

Specifically, SNPs are identified at positions 193 and 202 of exon 3, position 607 of exon 4, and positions 1020, 1021 and 1026 of exon 7 of KIR3DL1 alleles. Table 1 shows the SNPs and the allelic groups associated with the SNPs. The numbering of the nucleotide positions represent the nucleotide positions within the coding region of the protein in the absence of introns (i.e., the nucleotide numbering for ATG in the start codon in exon 1 is 1, 2, and 3, respectively, for A, T and G).

TABLE 1

| | Exon 3 | | Exon4 | Exon 7 | | |
|---|---|---|---|---|---|---|
| KIR3DL1 Alleles | Position 193 | Position 202 | Position 607 | Position 1020 | Position 1021 | Position 1026 |
| Null *004 Group | G | A | T | | | |
| Low *005 Group | A | A | T | | | |
| High *001 Group | A | A | C | | | |
| High *015 Group | A | G | C | C | A | G |
| Low *007 Group | A | G | C | C | G | G |
| KIR3DS1 Group | A | G | C | | | |

In accordance with this disclosure, the term "null*004 group" or "004 null group" includes KIR3DL1 null alleles *004, *019, *021, *036, *037, *039, *040, *056, *063 and *072.

The term "low *005 group" or "005 low group" includes KIR3DL1 low alleles *005, *041, *044, and *053.

The term "high *001 group" or "001 high group" includes KIR3DL1 high alleles *001, *016, *026, *027, *043, *052, *059, *060, *061, *064, *065, *067 and *075.

The term "high *002 group" or "002 high group" includes KIR3DL1 high alleles *002, *008, *015, *020, *006, *009, *017, *018, *022, *023, *024N, *025, *028, *029, *030, *031, *034, *035, *038, *051, *054, *057, *062, *066, *074, *076, and *077.

The term "low *007 group" or "007 low group" includes KIR3DL1 low alleles *007, *032 and *033.

The term "KIR3DS1 *013 group" includes KIR3DS1 alleles *013, *047, *010, *011, *012, *014, *045, *046, *048, *049N, *050, *055, and *058.

The SNPs present in exons 3 and 4 of KIR3DL1 alleles collectively allow for the division of KIR3DL1 alleles into four mutually-exclusive groups:

null*004 group,
low *005 group,
high *001 group, and
the remaining alleles: high *015 group, low *007 group, and KIR3DS1 *013 group.

See FIG. 1 and Table 1. The high *015 group and the KIR3DS1 *013 group can be distinguished based on the sizes of PCR products as further described herein below. The *007 low group is identified by relying additional SNPs in exon 6, which distinguish this group from the *015 high group.

Given this SNP-based grouping strategy, primers are designed to target SNPs identified herein and are paired to generate PCR products that enable KIR3DL1 allelic subgroup identification.

The term "primer", as used herein, means a synthetic oligonucleotide, typically designed for use in a nucleic acid hybridization assay or a polymerase chain reaction.

The term "primer pair" means a combination of a forward primer and a reverse primer for use in PCR.

Primers suitable for use in PCR should have a length that permits specific hybridization of the primers to their target DNA. Generally speaking, primers suitable for use in the method herein should have a length of at least 7, 8, 9 or 10 nucleotides, or preferably at least 11, 12, 13 or 14 nucleotides, or more preferably at least 15, 16, 17, or 18 nucleotides. Longer primers having 19, 20, 21, 22, 23, 24 or 25 nucleotides or more are also suitable for use herein. Typically, primers are not longer than 50 nucleotides, and preferably not longer than 40, 35, or 30 nucleotides.

In accordance with this disclosure, seven primers are designed to target or select SNPs identified for the KIR3DL1alleles. By "a primer targeting a SNP" it means that a primer binds to a nucleic acid region containing the SNP in a specific manner such that nucleic acids containing a particular nucleotide at the SNP position are amplified using this primer, and nucleic acids having a different nucleotide at the SNP position are not amplified using this primer.

For example, a first primer is designed as a reverse primer targeting the SNP at positions 193 in exon 3 of the KIR3DL1 alleles. This primer is designed to bind specifically to a region of exon 3 having G at position 193, a SNP unique to the null*004 group alleles. Thus, when this first primer is combined with a forward primer which binds to a conserved region of the KIR3DL1 alleles, the resulting PCR product can positively identify the presence of a null*004 group allele in the subject. For improved specificity, this first primer can be designed to have the nucleotide targeting (or base-pairing with) the SNP (G193) as close as possible to the 3' end of the primer sequence, for example, within 1-3 nucleotides. In specific embodiments, this first primer ends at its 3' end at position 193 (i.e., the nucleotide at the 3' end base pairs with G at position 193). In some embodiments, this first primer is designed to also target A at position 202; that is, the primer binds specifically to a region of exon 3 containing both G193 and A202. Examples of the first primer include any primer containing the sequence TGTGATTCC (SEQ ID NO: 12), such as CATGGAAGATGGGAATGTGGATTCC (SEQ ID NO: 13), for example.

A second primer is a forward primer targeting the SNP at position 193 in exon 3 of the KIR3DL1 alleles. This primer is designed to bind specifically to a region of exon 3 having A at position 193. Because A193 is shared among several allelic subgroups (low*005, high*001, high*015, low*007 and KIR3DS1), primers targeting additional SNPs are utilized in order to distinguish among these allelic groups, as further described below. Similar to the design of the first primer, the second primer is also designed to have the nucleotide targeting (or base-pairing with) the SNP (A193) as close as possible to the 3' end of the primer sequence, for example, within 1-3 nucleotides. In specific embodiments, this primer ends at its 3' end at position 193 (i.e., the nucleotide at the 3' end of the primer base pairs with A193). In some embodiments, the second primer is designed to also target A at position 202; that is, the primer binds specifically to a region of exon 3 containing both A193 and A202. Specific examples of the second primer include any primer containing the sequence AAAGAAGACA (SEQ ID NO: 14), such as CAATTTCATGCTATACAAAGAAGACA (SEQ ID NO: 15), for example.

A third primer is a reverse primer targeting the SNP at position 607 in exon 4 of the KIR3DL1 alleles. This primer is designed to bind specifically to a region of exon 4 having T at position 607. When combining the second primer (targeting A193) and the third primer targeting T607, this primer pair excludes all groups except for *005 (specificity against the null group is given by the forward primer (SNP at 193). Similar to the design of the first and second primers, the third primer is also designed to have the nucleotide targeting (or base-pairing with) the SNP (T607) as close as possible to the 3' end of the primer sequence, for example, within 1-3 nucleotides. In specific embodiments, this primer ends at its 3' end at position 607. Specific examples of the third primer include any primer containing the sequence GATAGGA (SEQ ID NO: 16), such as (G/A)GCTGACAACTGATAGGA (SEQ ID NO: 17) and GGG(G/A)GCTGACAACTGATAGGA (SEQ ID NO: 18), for example.

A fourth primer is a forward primer targeting the SNPs at position 193 and position 202 in exon 3 of the KIR3DL1 alleles. This primer is designed to bind specifically to a region of exon 3 having A at position 193 and A at position 202. Because A193 and A202 are shared between low*005 and high*001 groups, a reverse primer targeting the SNP at position 607 (the sixth primer below) is utilized to distinguish among these allelic groups, as further described below. The fourth primer is designed to have the nucleotide targeting (or base-pairing with) the SNP at 202 (A202) as close as possible to the 3' end of the primer sequence, for example, within 1-3 nucleotides. In specific embodiments, this primer ends at its 3' end at position 202 (i.e., the nucleotide at the 3' end base pairs with A at position 202). Specific examples of the fourth primer include any primer containing the sequence AGAATCCACA (SEQ ID NO: 19), such as GCTATACAAAGAAGACAGAATCCACA (SEQ ID NO: 20), for example.

A fifth primer is a forward primer and is designed to target the SNP at position 202 in exon 3; i.e., this primer is designed to bind specifically to a region of exon 3 of KIR3DL1 alleles having G at position 202. G202 is shared among high*015, low*007, and KIR3DS1 groups. Thus, a reverse primer targeting SNPs in exon 7 of KIR3DL1 alleles is utilized to identify the low*007 group alleles. The high*015 group and the KIR3DS1 group can be distinguished based on different sizes in PCR products. The fifth primer is designed to have the nucleotide targeting (or base-pairing with) the SNP at 202 (G202) as close as possible to the 3' end of the primer sequence, for example, within 1-3 nucleotides. In specific embodiments, this primer ends at its 3' end at position 202 (i.e., the nucleotide at the 3' end base pairs with G at position 202). In some embodiments, the fifth primer is designed to also target A at position 193. Specific examples of the fifth primer include any primer containing the sequence AGAATCCACG (SEQ ID NO: 21), such as CAAAGAAGACAGAATCCACG (SEQ ID NO: 22).

A sixth primer is a reverse primer and is designed to target the SNP at position 607 of exon 4. In particular, this sixth primer is designed to bind specifically to a region of exon 4 of KIR3DL1 alleles comprising C at position 607. This primer is designed to have the nucleotide targeting (or base-pairing with) C607 as close as possible to the 3' end of the primer sequence, for example, within 1-3 nucleotides. In specific embodiments, this primer ends at its 3' end at position 607 (i.e., the nucleotide at the 3' end base pairs with C at position 607). In some embodiments, the sixth primer is designed to also target T at position 624. Specific examples of the sixth primer include any primer containing the sequence ACTGATAGGG (SEQ ID NO: 23), such as AGCTGACAACTGATAGGG (SEQ ID NO: 24) and GGGAGCTGACAACTGATAGGG (SEQ ID NO: 25), for example.

A seventh primer is a reverse primer and designed to target the SNPs at positions 1020 and 1021 in exon 7. This primer is designed to bind specifically to a region of exon 7 of KIR3DL1 alleles having C at position 1020, and G at position 1021, and optionally also having G at position 1026. This primer is useful to distinguish the low*007 group from the high*015 group and the KIR3DS1*013 group alleles. Examples of the seventh primer include any primer containing the sequence CAGAACG (SEQ ID NO: 26), such as GAGGTCCCAATCAGAACG (SEQ ID NO: 27), for example.

Additional useful primers can be designed to permit primer pairing and performance of PCR reactions. For example, an eighth primer is also designed, which is a forward primer and binds to a conserved region of KIR alleles upstream of the region to which the first primer binds, and is used in combination with the first primer in a PCR reaction. A ninth primer is designed as a forward primer, which binds to a conserved region within intron 6 of KIR3DL1 and is used in combination with the seventh primer in PCR reactions. A "conserved region" means a region of KIR3DL1 which the KIR3DL1 alleles do not differ in sequences or show polymorphism.

Other useful primers include those for use as internal controls in PCR reactions. For example, control primers that amplify a 650 bp region from HLA-DR can be multiplexed into each reaction.

Primer Pairing and PCR Reactions

The primers described above are paired as follows to provide five primer pairs for use in five PCR reactions, which permit KIR3DL1 allele identification.

TABLE 2

| PCR Reactions | Primer Pair (Forward and Reverse) | Amplified KIR3DL1 Alleles |
| --- | --- | --- |
| Reaction 1 | F: eighth primer R: first primer | Null*004 Group |
| Reaction 2 | F: second primer R: third primer | Low*005 Group |
| Reaction 3 | F: fourth primer R: sixth primer | High*001 Group |
| Reaction 4 | F: fifth primer R: sixth primer | High*015 Group, Low*007 Group, and KIR3DS1*013 Group. (The amplification products for the High*015 Group and the KIR3DS1*013 Group can be distinguished based on size.) |
| Reaction 5 | F: ninth primer R: seventh primer | Low*007 Group |

Conditions for each of the five reactions can vary with respect to annealing temperature, extension time and number of cycles. Examples of suitable annealing temperatures for reactions 1-5 are: 66.9, 65.6, 68.5, 64.2 and 64.2, respectively. Acceptable variations in annealing temperature are −0.25 to +0.75° C. in annealing temperatures. Temperatures may vary according the specific PCR equipment used, depending on its current calibration, which can vary between machines, the quality of DNA preparation, or the reagents employed such as Taq, dNTP and specific PCR buffers. Examples of suitable extension time for reactions 1-5 are 3:30, 3:30, 3:45, 4:00 and 3:45 min, respectively. Reaction times may vary by −0:30 min and increased indefinitely. They vary based on the "ramp speed" of a PCR machine (the speed with which it changes between temperatures), the volume of a PCR reaction and the quality of DNA. Examples of cycles for reactions 1-5 are 30, 30, 35, 35 and 35, respectively. These examples represent optimized number of cycles to provide good resolution of DNA. However, the number of cycles can vary −10 to unlimited. The number of cycles may vary depending on the quality and quantity of input DNA, detection reagents and imaging threshold can impact the number of cycles used.

To perform the PCR reactions, a sample containing genomic DNA is taken from the subject being tested. The sample can be a tissue or blood sample, including, but not limited to, blood, fractions of blood, peripheral blood cells, skin or tissue biopsies, buccal swab samples, and umbilical cord blood. In some embodiments, the sample is processed to enrich or isolate genomic DNA, which serves as the template for the PCR reactions. Genomic DNA derived from subjects whose KIR3DL1 genotypes are known can be used as controls.

Identification of KIR3DL1 Alleles Based on Results from the PCR Reactions

In accordance with this disclosure, detection of an amplification product from the first PCR reaction indicates the presence of a KIR3DL1 null*004 group allele; detection of an amplification product from the second PCR reaction indicates the presence of a KIR3DL1*005-group low allele; detection of an amplification product from the third PCR reaction indicates the presence of a KIR3DL1*001-group high allele; detection of an amplification product from the fourth PCR reaction indicates the presence of one of a KIR3DL1*015-group high allele, a KIR3DL1*007-group low allele, or a KIR3DS1 allele; and detection of an amplification product from the fifth PCR reaction indicates the presence of a KIR3DL1 *007-group low allele. For example, control primers can be designed to provide a HLA-DR control band of about 0.6 kB; therefore, observation of an expected amplification product for a particular reaction, such as a product of an expected size between 1.4-2.1 kb, indicates positivity for that reaction.

Allelic identifications in a subject based on the results from the reactions permit classification of a subject into one of the functional groups, as described above. More specifically, detection of an amplification product from the first PCR reaction indicates the presence of a KIR3DL1-n (null)

allele, in which case the subject is assigned to the KIR3DL1-N functional group.

Figure 3:
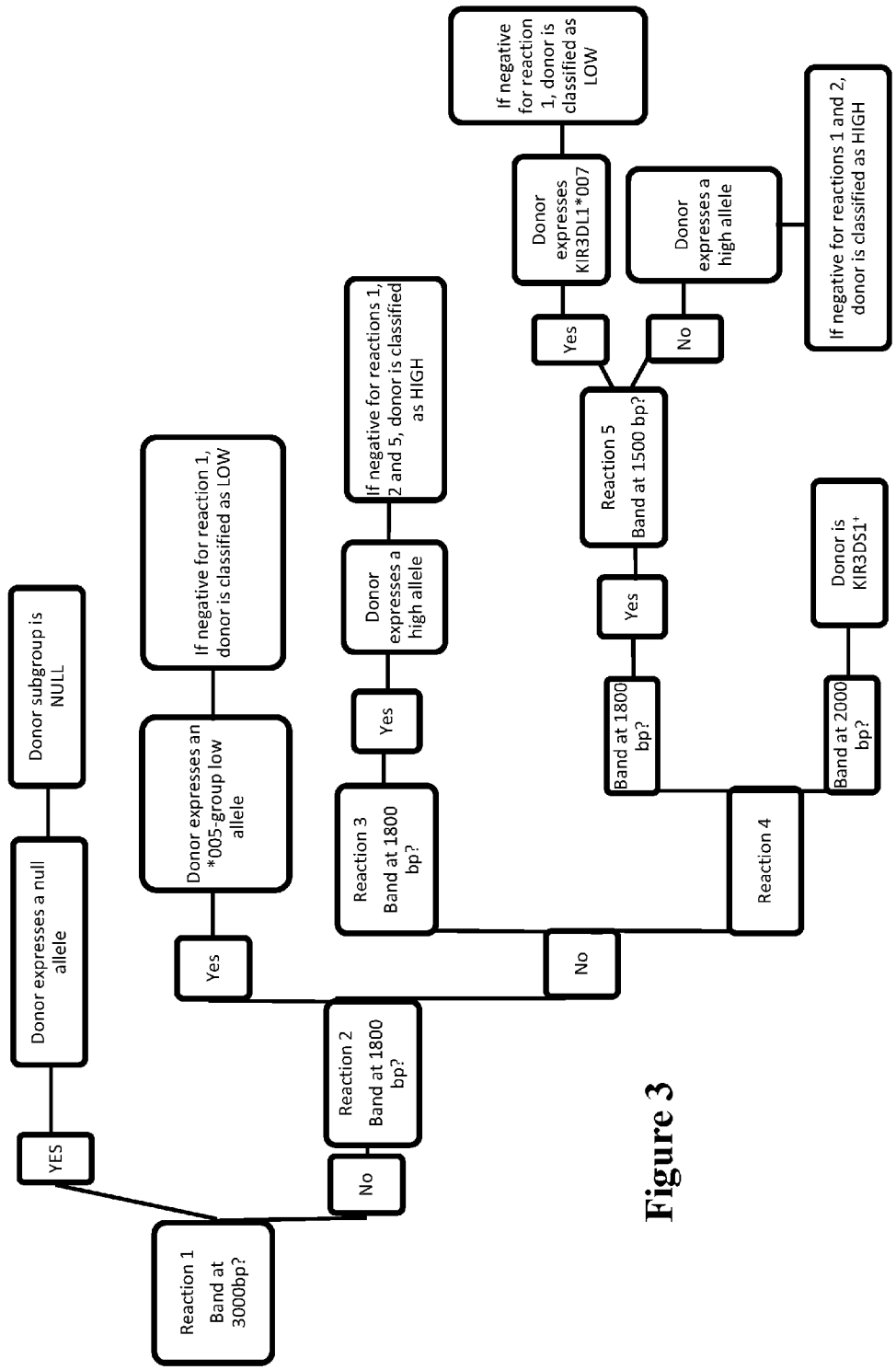
FIG. 3. Flow Chart for determining KIR3DL1 functional groups. Allele groupings are considered serially, from reactions 1-5. The order of precedence for allele grouping is null>low>high>3DS1.

Detection of an amplification product from the second reaction indicates the presence of a KIR3DL1-l (low) allele. If the subject is negative for the first reaction, then the subject is assigned to the to the KIR3DL1-L functional group. If no amplification product is detected from the second reaction, then the results from the third and fourth reactions are evaluated. If an amplification product is detected from the third PCR reaction, the subject expresses a KIR3DL1-h (high) allele, in which case, if no amplification product is detected from the first, second and fifth reaction (i.e., negative for null or low alleles), then the subject is assigned to the KIR3DL1-H functional group. If an amplification product is detected from the fourth reaction, the size of the amplification product is examined: a longer product indicates the presence of a KIR3DS1 allele, and a shorter product triggers further evaluation of the results from the fifth reaction, where an amplification product from the fifth reaction indicates the presence of a KIR3DL1-l (low) allele, and the patient is assigned to KIR3DL1-L, and the lack of a product from the fifth reaction indicates the presence of a KIR3DL1-h (high) allele, and the patient is assigned to KIR3DL1-H. FIG. 3 provides a flow chart illustrating the process for classifying a subject based on results from the five reactions.

A kit containing the above-described primers is also provided by this invention. The kit can include primer pairing instructions, or organized in a manner such that primer pairs are provided in separate compartments and properly labeled. The kit can also include instructions for PCR reactions and for interpretation of the results to permit KIR3DL1 classification of a subject.

Methods for assigning a KIR3DL1 functional group to a subject are also parts of this invention. The steps of such methods have been fully described above and are also illustrated in the following examples and in FIG. 3.

The methods, compositions and kits for classifying KIR3DL1 disclosed herein are useful in establishing prognoses. Diseases where HLA is deregulated, including but not limited to cancer, inflammatory bowel disease, conditions or infections associated with HIV, cytomegalovirus, hepatitis B virus, human papillomavirus and influenza, will likely be influenced by compound allotypes of KIR3DL1 and HLA-B. The methods, compositions and kits for classifying KIR3DL1 disclosed herein are also useful in selection of the most appropriate stem cell donor for allergenic HCT for acute myelogenous leukemia patients.

The present description is further illustrated by the following examples, which should not be construed as limiting in any way. The contents of all cited references (including literature references, issued patents, and published patent applications as cited throughout this application) are hereby expressly incorporated by reference.

EXAMPLES

Example 1

Materials and Methods
KIR3DL1 Allele Coding Sequences

KIR3DL1 allele coding sequences were downloaded from the EMBL-EBI IPD KIR database. All alleles for which coding sequences are available were included in our alignment analyses and suballeles differing exclusively within intronic regions were classed with their canonical allele. Gene alignments were performed using MacVector software version 12.0 and the relevant exon regions aligned are shown in FIG. 1.

Grouping Strategy and Primer Design

The KIR3DL1 allotypes of 426 donors were determined by genomic sequencing (Belle et al., *Tissue Antigens* 71:434-439 (2008); Jiang et al., *Tissue Antigens* 76(1): 64-6 (2010); Lebedeva et al., *HIM* 68:789-796 (2007); Levinson et al., *Genes Immun* 9:249-258 (2008)). Among this cohort, 11 alleles accounted for greater than 98% frequency, and were therefore prioritized in the assessment of subgroup-specific SNPs.

KIR3DL1 allelic subgroups have been classified based on the density with which Z27 and DX9 antibodies bind, a feature that is correlated to their interactions with HLA-Bw4 alleles. The null alleles (*004, *019) are retained intracellularly, and cannot be detected by surface staining with either antibody (4). The low (*005, 007) and high (*001, 002, 008, 015, 020) alleles of KIR3DL1 bind both DX9 and Z27 antibodies with high and low densities, respectively (Gardiner et al., *Journal of Immunology* 166:2992-3001 (2001); Yawata et al., *J Exp Med* 203:633-645 (2006)). Finally, the activating KIR3DS1 alleles, typified by KIR3DL1*013, are bound weakly only by Z27, and unbound by DX9 (Pascal et al., *Journal of Immunology* 179:1625-1633 (2007); Trundley et al., *Eur J Immunol* 37:780-787 (2007)).

Two polymorphic regions, present in exons 3 and 4, collectively allowed for the division of KIR3DL1 alleles into four mutually-exclusive groups (FIG. 1). Under this scheme, the *007-group of low alleles was amplified among the *015 group of high alleles. Accordingly, a fifth reaction was created to allow their positive identification as "low" group alleles (Yawata et al., *J Exp Med* 203:633-645 (2006)).

The surface density and signaling capacities for the low-frequency KIR3DL1 alleles are unknown. However, as these alleles accounted for fewer than 2% of our patient cohort, supervised group assignments were neither possible nor justified. Instead, the remaining KIR3DL1 alleles were stratified into allelic groups based on sequence similarity within the indicated regions (FIG. 1). Division of low-frequency alleles in this manner yielded groups consistent with their phylogenetic associations to high frequency alleles (Parham et al., *The Journal of Immunology* 187:11-19 (2011)).

Pairs of primers targeting SNPs consistent among allele subgroups were identified, and their specificity for KIR3DL1 was confirmed using NCBI primer blast. A 0.6 kb control band, derived from a conserved region of HLA-DR, was multiplexed into each reaction (Table 3) (Vilches et al., *Tissue Antigens* 75:415-422 (2007)).

Optimization of PCR Reactions

PCR conditions were optimized using Applied Biosystems PCR System 9700 and Eppendorf Mastercycler epGradient thermocyclers. 50 ng of DNA was included in each 25 µL reaction, prepared with Taq polymerase, dNTP and PCR buffer according to the manufacturer's instructions (Roche, Nutley, N.J.). Control and allele-specific primer concentrations were optimized independently for each reaction to provide maximum specificity and consistent allele group-specific amplification (Table 3). DNA, whose KIR3DL1 allotypes were known from genomic sequencing (Giglio et al. (November 2012)), was used to optimize reaction conditions.

Results and Validation

Identification of donor KIR3DL1 allelic subgroups was achieved using five PCR reactions (FIG. 2). The combination of results identifies the allelic subgroups of each of the alleles present in a donor. In patients expressing more than one inhibitory allele, functional groups can be determined by hierarchical exclusion, with null ranking highest, followed by low then high according to previous clinical findings (Martin et al., *Nature Genetics* 39:733-740 (2007); Giglio et al. (November 2012)).

Identification of the NULL and *007 Functional Groups of Alleles by Group-Defining SNPs The null group of alleles was identified using a reverse primer that selects for a unique G→T SNP (position 193), coupled with a forward primer that targets an upstream, conserved region of KIR (Hsu et al., *The Journal of Immunology* 169:5118-5129 (2002)). Similarly, the *007 group of low alleles was identified using a unique SNP present in exon 7 at position 1020. Due to large introns flanking this short exon, a primer specific to a conserved, non-coding region was used. Given that grouping priority was given to low over high density alleles, and that *007-group alleles would give positive reactions for both high and *007, donors found to express *007, in the absence of a null allele, were classified as low.

Identification of the Low*005 and High Functional Subgroups of KIR3DL1 Alleles

Overlapping homology between low, high and 3DS1 alleles at positions 202 and 607 precluded targeting a single SNP to identify the remaining KIR3DL1 allelic subgroups. Instead, the inventors applied an exclusionary approach, wherein neither the forward nor reverse primers were subgroup-specific, but only alleles within a given allelic group were targeted by both primers in a single reaction.

First, the identification of *005-group low alleles utilized a forward primer that targets a SNP present in high, 3DS1 and 005-group low alleles. Specificity for the *005-group low alleles was provided in combination with a reverse primer that hybridized with null and 005-group low alleles.

Two reactions are used to identify the high expression allele subgroup. The first used a forward primer whose specificity was shared with the *001, *005 and null groups of alleles. In combination with a reverse primer that targeted all high and KIR3DS1 alleles, the resulting product positively identified the *001 group of high-expression alleles. The *015 group high alleles and KIR3DS1 were identified using the same reverse primer together with a forward primer specific to this subgroup. Owing to a 300 bp difference in the size of the intron separating exons three and four among the activating and inhibitory alleles, KIR3DL1 high and KIR3DS1 alleles were easily distinguished as 1.7 and 2.0 kb amplicons, respectively.

Examples of specific reaction master mixes and conditions are set forth below.

TABLE 3

Primers and reaction conditions for identification of KIR3DL1 functional allele subgroups. Five reactions allow for assignment of donors to null, low and high inhibition groups. Control primers, specific to HLA-DR, are multiplexed into each reaction as a DNA loading control and competing reaction to enhance the stringency of PCR reactions. The reaction targeting both the *015-group high alleles and KIR3DS1, however, these alleles are easily distinguished owing to a larger intron among the activating alleles

| Reaction | Primer sequence 5'→3' | Amplicon size (kB) | Vol. Control primers (pm) | Vol. Allele-specific primer (pm) | Annealing temp | Extension time | Number of cycles |
|---|---|---|---|---|---|---|---|
| Null | ConsF: ATCCTGTGCGCTGCTGAGCTGAG (SEQ ID NO: 28) 004R: CATGGAAGATGGGAATGTGGATTCC (SEQ ID NO: 13) | 2 | 1.65 | 19.00 | 66.9° C. | 3:30 | 30 |
| *005-group Low | F2D: CAATTTCATGCTATACAAAGAAGACA (SEQ ID NO: 15) R1E: GGGRGCTGACAACTGATAGGA (SEQ ID NO: 18) | 1.6 | 1.65 | 19.00 | 65.6° C. | 3:30 | 30 |
| *001-group High | F2B: GCTATACAAAGAAGACAGAATCCACA (SEQ ID NO: 20) R2D: GGGAGCTGACAACTGATAGGG (SEQ ID NO: 25) | 1.6 | 4.13 | 19.00 | 68.5° C. | 3:45 | 35 |
| *015 group High, KIR3DS1 group, *007 Low | F3D: CAAAGAAGACAGAATCCACG (SEQ ID NO: 22) R2D: GGGAGCTGACAACTGATAGGG (SEQ ID NO: 25) | 3DL1:1.6 3DS1:1.9 | 1.65 | 19.00 | 64.2° C. | 4:00 | 35 |

TABLE 3-continued

Primers and reaction conditions for identification of KIR3DL1 functional allele subgroups. Five reactions allow for assignment of donors to null, low and high inhibition groups. Control primers, specific to HLA-DR, are multiplexed into each reaction as a DNA loading control and competing reaction to enhance the stringency of PCR reactions. The reaction targeting both the *015-group high alleles and KIR3DS1, however, these alleles are easily distinguished owing to a larger intron among the activating alleles

| Reaction | Primer sequence 5'→3' | Amplicon size (kB) | Vol. Control primers (pm) | Vol. Allele-specific primer (pm) | Annealing temp | Extension time | Number of cycles |
|---|---|---|---|---|---|---|---|
| *007-group Low | F4D-3: CAGAGATCTGTGCCAGC (SEQ ID NO: 29) R6D-5: GAGGTCCCAATCAGAACG (SEQ ID NO: 27) | 1.4 | 2.06 | 18.60 | 64.2° C. | 3:45 | 35 |
| Control HLA-DR | GAGGTAACTGTGCTCACGAACAGC (SEQ ID NO: 30) CACGTTCTCTGTAGTCTCTGGG (SEQ ID NO: 31) | 0.6 | | | | | |

| Reaction 1 | 66.9° C. annealing | |
|---|---|---|
| 30 cycles | 3:30 min extension at 68° C. | |
| Master mixes | Vol/reaction | For # of reactions |
| | Per Sample | 30 |
| PCR buffer | 2.5 | 75 |
| dNTP | 0.5 | 15 |
| 004R | 0.575 | 17.25 |
| ConsF | 0.575 | 17.25 |
| 633 (0.33X) | 0.05 | 1.5 |
| 360 (0.33X) | 0.05 | 1.5 |
| Taq | 0.25 | 7.5 |
| dH2O | 17.5 | 525 |

Reaction 1 amplifies Nulls
High-frequency alleles:

004
019

Low frequency alleles:

021
036
037
039
040
056
063
072

Amplicon size: 3000 bp

| Reaction 2 | 65.6° C. annealing | |
|---|---|---|
| 30 cycles | 3:30 min extension at 68° C. | |
| Master mixes | Vol/reaction | For # of reactions |
| | Per Sample | 30 |
| PCR buffer | 2.5 | 75 |
| dNTP | 0.5 | 15 |
| F2D | 0.575 | 17.25 |
| R1E | 0.575 | 17.25 |
| 633 (0.33X) | 0.05 | 1.5 |
| 360 (0.33X) | 0.05 | 1.5 |
| Taq | 0.25 | 7.5 |
| dH2O | 18 | 540 |

Reaction 2 amplifies LOWs:

High-frequency alleles:

005

Low frequency alleles:

041
044
053

Amplicon size: 1700 bp

| Reaction 3 | 68.5° C. annealing | |
|---|---|---|
| 35 cycles | 3:45 min extension at 69° C. | |
| Master mixes | Vol/reaction | For # of reactions |
| | Per Sample | 30 |
| PCR buffer | 2.5 | 75 |
| dNTP | 0.5 | 15 |
| F2B | 0.575 | 17.25 |
| R2D | 0.575 | 17.25 |
| 633 (0.33X) | 0.125 | 3.75 |
| 360 (0.33X) | 0.125 | 3.75 |
| Taq | 0.25 | 7.5 |
| dH2O | 18 | 540 |

Reaction 3 amplifies SOME HIGHs:

High-frequency alleles:

001
016

Low frequency alleles:

h*052
026
027
043
059
060
061
064
065
067
073

Amplicon size: 1700 bp

| Reaction 4 | 64.2° C. annealing | |
|---|---|---|
| 35 cycles | 4:00 min extension at 68° C. | |
| Master mixes | Vol/reaction Per Sample | For # of reactions 30 |
| PCR buffer | 2.5 | 75 |
| dNTP | 0.5 | 15 |
| F3D | 0.575 | 17.25 |
| R2D | 0.575 | 17.25 |
| 633 (0.33X) | 0.05 | 1.5 |
| 360 (0.33X) | 0.05 | 1.5 |
| Taq | 0.25 | 7.5 |
| dH2O | 18 | 540 |

Reaction 4 amplifies OTHER HIGHs:

High-frequency alleles:

002
015
009***
008
020
007*

Low-frequency alleles:

| 025 | 006* |
| 030 | 028* |
| 031 | 029* |
| 033 | 017 |
| 038 | 018 |
| 054 | 023 |
| 057 | 024N |
| 062 | 068 |
|     | 066 |

Amplicon size: 1700 bp

| Reaction 5 | 64.2° C. annealing | |
|---|---|---|
| 35 cycles | 3:45 min extension at 72° C. | |
| Master mixes | Vol/reaction Per Sample | For # of reactions 30 |
| PCR buffer | 2.5 | 75 |
| dNTP | 0.5 | 15 |
| F4D-3 | 0.5625 | 16.875 |
| R6D-5 | 0.5625 | 16.875 |
| 633 (0.33X) | 0.0625 | 1.875 |
| 360 (0.33X) | 0.0625 | 1.875 |
| Taq | 0.25 | 7.5 |
| dH2O | 17.85 | 535.5 |

Reaction 5 amplifies 007:

High frequency alleles:

007

Low frequency alleles:

032** (**032 is a high allele, low population frequency)
033

Amplicon size: 1500 bp

---

```
<160> NUMBER OF SEQ ID NOS: 31

<210> SEQ ID NO 1
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 1
acaatttcat gctatacaaa gaagacggaa tccacattcc catcttccat ggc          53

<210> SEQ ID NO 2
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 2
acaatttcat gctatacaaa gaagacagaa tccacattcc catcttccat ggc          53

<210> SEQ ID NO 3
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 3
acaatttcat gctatacaaa gaagacagaa tccacgttcc catcttccat ggc          53

<210> SEQ ID NO 4
<211> LENGTH: 25
```

```
<212> TYPE: DNA
<213> ORGANISM: Artificial Sequence
<220> FEATURE:
<223> OTHER INFORMATION: Synthetic Oligonucleotide

<400> SEQUENCE: 4
cctcctatca gttgtcagct cccag                                                25

<210> SEQ ID NO 5
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 5
cctcctatca gttgtcagcc cccag                                                25

<210> SEQ ID NO 6
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 6 cccctatca gttgtcagct cccag                                                 25

<210> SEQ ID NO 7
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 7
ccacctatca gttgtcagct cccag                                                25

<210> SEQ ID NO 8
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 8
catgttctca ttgggacctc agtggtc                                              27

<210> SEQ ID NO 9
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 9
cacattctga ttgggacctc agtggtc                                              27

<210> SEQ ID NO 10
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 10
```

```
catgttctga ttgggacctc agtggtc                                              27

<210> SEQ ID NO 11
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 11
cacgttctga ttgggacctc agtggtc                                              27

<210> SEQ ID NO 12
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 12
tgtggattcc                                                                 10

<210> SEQ ID NO 13
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 13
catggaagat gggaatgtgg attcc                                                25

<210> SEQ ID NO 14
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 14
aaagaagaca                                                                 10

<210> SEQ ID NO 15
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 15
caatttcatg ctatacaaag aagaca                                               26

<210> SEQ ID NO 16
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 16 gatagga                                                                     7

<210> SEQ ID NO 17
<211> LENGTH: 18
<212> TYPE: DNA
<213> ORGANISM: Artificial Sequence
```

<220> FEATURE:
<223> OTHER INFORMATION: Synthetic Oligonucleotide

<400> SEQUENCE: 17
rgctgacaac tgatagga                                                      18

<210> SEQ ID NO 18
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 18
gggrgctgac aactgatagg a                                                  21

<210> SEQ ID NO 19
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 19
agaatccaca                                                               10

<210> SEQ ID NO 20
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 20
gctatacaaa gaagacagaa tccaca                                             26

<210> SEQ ID NO 21
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 21
agaatccacg                                                               10

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
caaagaagac agaatccacg                                                    20

<210> SEQ ID NO 23
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 23
actgataggg                                                               10

```
<210> SEQ ID NO 24
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 24
agctgacaac tgataggg                                                 18

<210> SEQ ID NO 25
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 25
gggagctgac aactgatagg g                                             21

<210> SEQ ID NO 26
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 26 cagaacg                                                              7

<210> SEQ ID NO 27
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 27
gaggtcccaa tcagaacg                                                 18

<210> SEQ ID NO 28
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 28
atcctgtgcg ctgctgagct gag                                           23

<210> SEQ ID NO 29
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 29
cagagatctg tgccagc                                                  17

<210> SEQ ID NO 30
<211> LENGTH: 24
<212> TYPE: DNA
<213> ORGANISM: Artificial Sequence
<220> FEATURE:
<223> OTHER INFORMATION: Synthetic Oligonucleotide
```

```
<400> SEQUENCE: 30
gaggtaactg tgctcacgaa cagc                                          24

<210> SEQ ID NO 31
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 31
cacgttctct gtagtctctg gg                                            22
```

What is claimed is:

1. A method of classifying KIR3DL1 alleles in a subject, comprising
performing five PCR reactions on a genomic DNA sample obtained from the subject wherein
a first reverse primer comprising the sequence of SEQ ID NO: 12 and a first forward primer comprising the sequence of SEQ ID NO: 28 provide a primer pair for a first PCR reaction;
a second reverse primer comprising the sequence of SEQ ID NO: 16 and a second forward primer comprising the sequence of SEQ ID NO: 14 provide a primer pair for a second PCR reaction;
a third reverse primer comprising the sequence of SEQ ID NO: 23 and a third forward primer comprising the sequence of SEQ ID NO: 19 provide a primer pair for a third PCR reaction;
a fourth reverse primer comprising the sequence of SEQ ID NO: 23 and a fourth forward primer comprising the sequence of SEQ ID NO: 21 provide a primer pair for a fourth PCR reaction; and
a fifth reverse primer comprising the sequence of SEQ ID NO: 26 and a fifth forward primer comprising the sequence of SEQ ID NO: 29 provide a primer pair for a fifth PCR reaction; and
determining the KIR3DL1 alleles present in the subject based on detection of amplification products from the five PCR reactions, wherein
the presence of an amplification product from the first PCR reaction indicates the presence of a KIR3DL1-null allele;
the presence of an amplification product from the second PCR reaction indicates the presence of a KIR3DL1 *005-group low allele;
the presence of an amplification product from the third PCR reaction indicates the presence of a KIR3DL1 *001-group high allele;
the presence of an amplification product from the fourth PCR reaction indicates the presence of one of a KIR3DL1 *015-group high allele, a KIR3DL1 *007-group low allele, or a KIR3DS1 allele; and
the presence of an amplification product from the fifth PCR reaction indicates the presence of a KIR3DL1 *007-group low allele.

2. The method of claim 1, wherein the subject is assigned to a KIR3DL1 functional group in accordance with detection of amplification products from the five PCR reactions, wherein said functional group is selected from the group consisting of KIR3DL1-N, KIR3DL1-L and KIR3DL1-H.

3. The method of claim 1, wherein the subject is assigned to the KIR3DL1-N functional group based on the presence of an amplification product from the first PCR reaction.

4. The method of claim 1, wherein the subject is assigned to the KIR3DL1-L functional group based on the absence of an amplification product from the first PCR reaction and the presence of an amplification product from the second PCR reaction.

5. The method of claim 1, wherein the subject is assigned to the KIR3DL1-L functional group based on the absence of an amplification product from the first and second PCR reactions, the presence and size of an amplification product from the fourth PCR reaction, and the presence of an amplification product from the fifth PCR reaction.

6. The method of claim 1, wherein the subject is assigned to the KIR3DL1-H functional group based on the absence of an amplification product from the first, second and fifth PCR reactions, and the presence of an amplification product from the third PCR reaction.

7. The method of claim 1, wherein the subject is assigned to the KIR3DL1-H functional group based on the presence and size of an amplification product from the fourth PCR reaction, and the absence of an amplification product from the first, second, and fifth PCR reactions.

8. The method of claim 1, wherein the sequence of the first reverse primer is SEQ ID NO: 13.

9. The method of claim 1, wherein the first reverse primer specifically binds to a region of exon 3 of KIR3DL1 alleles.

10. The method of claim 1, wherein the first forward primer specifically binds to a conserved region upstream of exon 3 of KIR3DL1 alleles.

11. The method of claim 1, wherein the sequence of the second forward primer is SEQ ID NO: 15.

12. The method of claim 1, wherein the second forward primer specifically binds to a region of exon 3 of KIR3DL1 alleles.

13. The method of claim 1, wherein the sequence of the second reverse primer is SEQ ID NO: 17 or SEQ ID NO: 18.

14. The method of claim 1, wherein the second reverse primer specifically binds to a region of exon 4 of KIR3DL1 alleles.

15. The method of claim 1, wherein the sequence of the third forward primer is SEQ ID NO: 20.

16. The method of claim 1, wherein the third forward primer specifically binds to a region of exon 3 of KIR3DL1 alleles.

17. The method of claim 1, wherein the sequence of the third reverse primer is SEQ ID NO: 24 or SEQ ID NO: 25.

18. The method of claim 1, wherein the third reverse primer specifically binds to a region of exon 4 of KIR3DL1 alleles.

19. The method of claim 1, wherein the sequence of the fourth forward primer is SEQ ID NO: 22.

20. The method of claim 1, wherein the fourth forward primer specifically binds to a region of exon 3 of KIR3DL1 alleles.

21. The method of claim 1, wherein the sequence of the fourth reverse primer is SEQ ID NO: 24 or SEQ ID NO: 25.

22. The method of claim 1, wherein the fourth reverse primer specifically binds to a region of exon 4 of KIR3DL1 alleles.

23. The method of claim 1, wherein the fifth forward primer specifically binds to a conserved region within intron 6 of KIR3DL1 alleles.

24. The method of claim 1, wherein the sequence of the fifth reverse primer is SEQ ID NO: 27.

25. The method of claim 1, wherein the fifth reverse primer specifically binds to a region of exon 7 of KIR3DL1 alleles.

26. The method of claim 1, wherein the presence of a 2 kb amplification product from the fourth PCR reaction indicates the presence of a KIR3DS1 allele.

27. The method of claim 1, wherein the presence of a 1.7 kb amplification product from the fourth PCR reaction and the presence of an amplification product from the fifth PCR reaction indicates the presence of a KIR3DL1 *007-group low allele.

28. The method of claim 1, wherein the presence of a 1.7 kb amplification product from the fourth PCR reaction and the absence of an amplification product from the fifth PCR reaction indicates the presence of a KIR3DL1 *015-group high allele.

* * * * *